United States Patent [19]

Adiutori

[11] Patent Number: 4,902,139
[45] Date of Patent: Feb. 20, 1990

[54] APPARATUS AND METHOD FOR MEASURING THE THERMAL PERFORMANCE OF A HEATED OR COOLED COMPONENT

[75] Inventor: Eugene F. Adiutori, Westchester, Ohio

[73] Assignee: General Electric Company, Cincinnati, Ohio

[21] Appl. No.: 180,919

[22] Filed: Apr. 13, 1988

[51] Int. Cl.⁴ .................. G01N 25/00; G01N 25/11; G01K 13/02

[52] U.S. Cl. .................................... 374/137; 374/29; 374/144

[58] Field of Search ................ 374/29, 44, 137, 124, 374/144; 219/201

[56] References Cited

U.S. PATENT DOCUMENTS

| | | | |
|---|---|---|---|
| 1,528,383 | 3/1925 | Schmidt | 374/30 |
| 2,585,934 | 2/1952 | Haswell . | |
| 3,123,996 | 3/1964 | Musial . | |
| 3,290,482 | 12/1966 | Dodd et al. | 219/201 |
| 3,592,061 | 7/1971 | Schwedland et al. . | |
| 3,623,368 | 11/1971 | Decker . | |
| 3,672,204 | 6/1972 | Green . | |
| 3,715,923 | 2/1973 | Hornbaker et al. | 374/134 |
| 4,024,751 | 5/1977 | Potrzebowski | 374/43 |
| 4,192,989 | 3/1980 | Jeromin | 219/201 X |
| 4,208,574 | 6/1980 | Schafer | 219/201 X |
| 4,384,793 | 5/1983 | O'Brien | 374/115 |
| 4,504,156 | 3/1985 | Currie et al. | 374/45 |
| 4,526,732 | 7/1985 | Kakii et al. | 219/201 X |
| 4,595,298 | 6/1986 | Frederick . | |
| 4,630,938 | 12/1986 | Palczewska | 374/43 X |
| 4,644,162 | 2/1987 | Bantel et al. . | |
| 4,684,265 | 8/1987 | Bourrelly et al. | 374/43 |
| 4,738,549 | 4/1988 | Plimpton | 374/208 |
| 4,779,994 | 10/1988 | Diller et al. | 374/29 |

FOREIGN PATENT DOCUMENTS

| | | | |
|---|---|---|---|
| 0400821 | 1/1974 | U.S.S.R. | 374/137 |
| 1319865 | 6/1973 | United Kingdom | 374/29 |

*Primary Examiner*—Daniel M. Yasich
*Attorney, Agent, or Firm*—Jerome C. Squillaro; Steven J. Rosen

[57] ABSTRACT

The thermal performance of cooling circuits for cooled components, such as turbine blades used in gas turbine engines, may be determined by applying a known amount of heat flux to a predetermined surface of the component, directing a cooling fluid flow having predetermined characteristics through the cooling circuit of the component, and measuring a temperature distribution on a preselected surface of the component.

The thermal performance of heating circuits for heated components, such as those involved in clearance control in a gas turbine engine, or other components in which a controlled thermal contraction or expansion is desired, may be determined by applying a known amount of heat flux to a predetermined surface of the component, applying a cooling fluid flow having predetermined characteristics to the heating circuits, and measuring a temperature distribution on a preselected surface of the component.

42 Claims, 5 Drawing Sheets

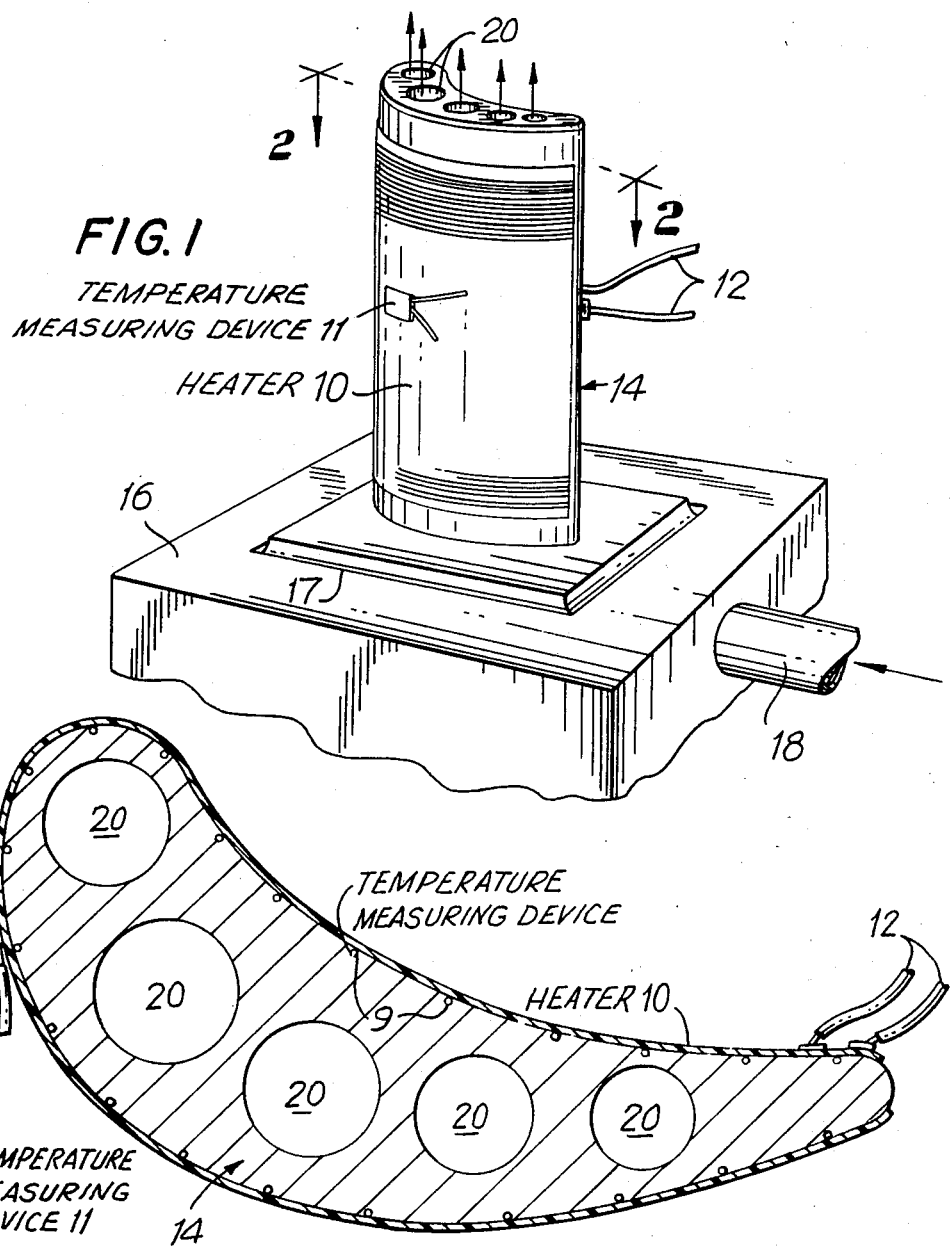

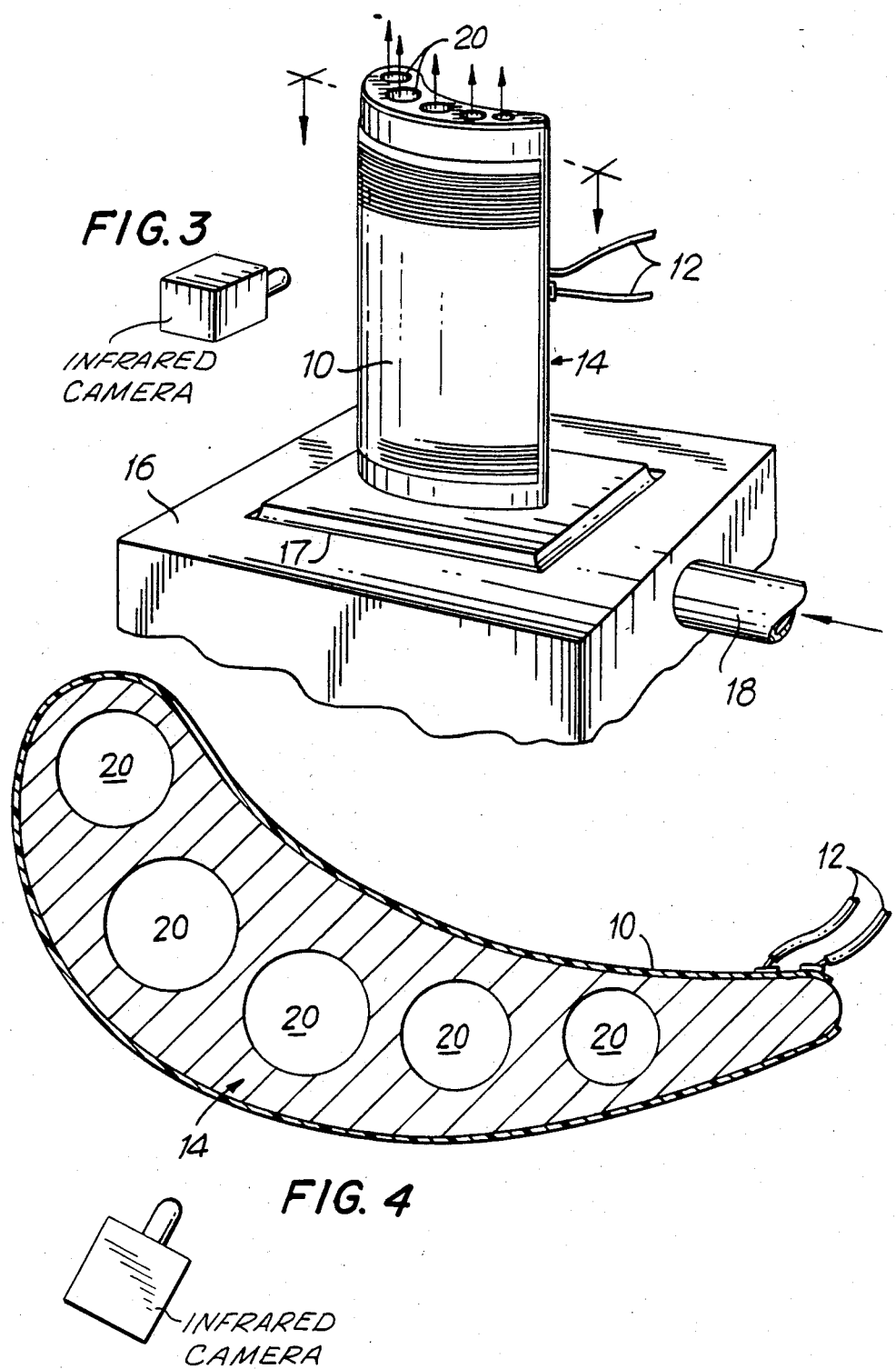

APPARATUS AND METHOD FOR MEASURING THE THERMAL PERFORMANCE OF A HEATED OR COOLED COMPONENT

FIELD OF THE INVENTION

This invention relates to heated or cooled components. More particularly, it relates to an apparatus and method for measuring the thermal performance of components exposed to heating or cooling fluid. Although the invention is useful in many different applications, it is especially useful for measuring the thermal performance of components having internal heating or cooling circuits.

CROSS REFERENCE TO RELATED PATENT APPLICATIONS

Application Ser. No. 180,986, filed Apr. 13, 1988, of Eugene F. Adiutori, entitled "METHOD AND APPARATUS FOR MEASURING THE DISTRIBUTION OF HEAT FLUX AND HEAT TRANSFER COEFFICIENTS ON THE SURFACE OF A COOLED COMPONENT USED IN A HIGH TEMPERATURE ENVIRONMENT."

Application Ser. No. 181,128, filed Apr. 13, 1988 of Eugene F. Adiutori and James E. Cahill, entitled "APPARATUS AND METHOD FOR DETERMINING HEAT TRANSFER COEFFICIENT BASED ON TESTING ACTUAL HARDWARE RATHER THAN SIMPLISTIC SCALE MODELS OF HARDWARE."

BACKGROUND OF THE INVENTION

It is well known to provide mechanical components, such as those found in gas turbine engines, with cooling circuits or systems in order to permit operation of machinery containing those components at temperatures higher than would be possible without such cooling systems. The higher operating temperatures permitted by such cooling systems result in improved performance and efficiency without damage to the cooled components.

In order to realize such improved performance and efficiency, gas turbine engines have cooling circuits associated with selected critical components in the engine. Examples of cooling circuits in a gas turbine engine include a series of cooling passages inside critical components, such as turbine blades, vanes, and shrouds. During the operation of the engine, a cooling fluid is passed through these passages to enable the components to withstand temperatures which would otherwise damage or destroy them.

The first prototype of a gas turbine engine design sometimes fails because of a design or manufacturing defect in the cooling circuits associated with critical cooled components. To minimize the likelihood of such an occurrence, it would be desirable to measure the thermal performance of the cooling circuits in those critical components as soon as the first of those components is made. The results of this measurement would be used to determine whether or not the actual thermal performance of the cooling circuit agrees closely with predicted performance and whether or not a cooling circuit design meets the cooling requirements of the component in which it is to be used.

At the present time, these measurements are not obtained because no practical way of obtaining them is known. Consequently, the first prototype of an engine design is always operated with no prior measurements of the actual thermal performance of the cooling circuits.

In addition to a need for measuring the thermal performance of cooling circuits as described above, there is also a need to exercise process control in the manufacture of critical cooled components once a cooling circuit design has been decided upon. Specifically, there is a need to verify that each cooled component and its cooling circuit has the required thermal performance. This could be accomplished by measuring the actual or as-built thermal performance of each component and its cooling circuit. As in the case of comparing the actual performance of the cooling circuits against design predictions, there is no practical way of doing this at the present time.

In addition to providing cooling passages in selected components, other components in gas turbine engines have passages through which heating fluid is passed to selectively heat those components. For example, selected portions of a gas turbine engine may be heated to control thermal expansion of those portions of the engine. This would be desirable in a situation such as a system for controlling the clearance between the tips of the blades in the compressor or turbine and the casing surrounding the blades. It would also be desirable in a situation where it was necessary to maintain the temperature of two parts of the engine the same to avoid thermal stresses and the like.

In the past, no effort was made to measure the actual or as-built thermal performance of cooling or heating circuits until a prototype engine was built, instrumented, and operated. There are at least two significant drawbacks in relying only on such engine tests to confirm as-built thermal performance. One, failure of the heating or cooling circuits to satisfy their design intent can and sometimes does result in damaging or destroying the engine in which they are operated. Two, the length of the design cycle from initial design of the heating or cooling circuits to actual verification of the adequacy of their performance can be many years.

Consequently, a need exists for a test which will permit the thermal performance of the heating or cooling circuit of an engine component to be measured as soon as the first component is actually fabricated, before it is installed and operated in an engine. This may be accomplished in accordance with the invention of this application by measuring the temperature distribution on a preselected surface of the component when the component is exposed to cooling fluid flow having predetermined characteristics, such as one or more of a predetermined flow rate, pressure, and temperature.

SUMMARY OF THE INVENTION

The invention of this application involves an apparatus and method for checking the thermal performance of a heating or cooling circuit of a cooled component which meets the need mentioned above. In accordance with one example of the invention, a heater applies a predetermined amount of heat flux to a surface of the component to be tested and a flow fixture applies a cooling fluid flow having predetermined characteristics to a cooling circuit inside the component. A measuring device measures the temperature distribution on a preselected surface of the cooled component to provide an indication of the thermal performance of the cooling circuit.

In a situation where the performance of a heating circuit is to be checked, cooling fluid flow having predetermined characteristics is applied to the heating circuit and a predetermined heat flux is applied to a predetermined surface of the component. The temperature distribution on a preselected surface of the component is measured to provide an indication of the thermal performance of the heating circuit.

BRIEF DESCRIPTION OF THE DRAWINGS

FIG. 1 is a perspective view of a turbine blade being tested in accordance with the principles of the invention of this application.

FIG. 2 is a cross section of the turbine blade of FIG. 1 taken along line 2—2 in FIG. 1.

FIGS. 3 and 4 are a perspective view and a cross section, respectively, which illustrate the use of an infrared camera to indirectly measure the surface temperature distribution on the surface of a turbine blade similar to the turbine blade depicted in FIGS. 1 and 2.

DETAILED DESCRIPTION OF THE INVENTION

Figure 5:
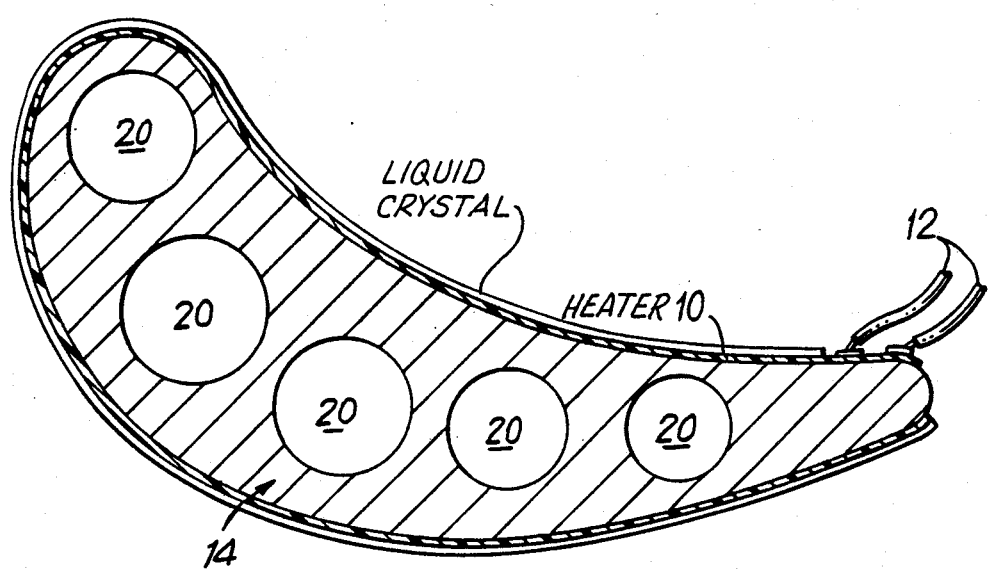
FIG. 5 is a cross section which illustrates the use of liquid crystal paint to measure the surface temperature distribution on the surface of a turbine blade similar to the turbine blades depicted in FIGS. 1–4.

FIG. 1 shows one example of the invention, an arrangement for measuring or checking the thermal performance of a cooling circuit in a turbine blade 14 used in a gas turbine engine. In order to accomplish this thermal check, a number of temperature measuring devices is attached to, or embedded in, the exterior surface of the blade and distributed in such a manner over the surface of the blade that measurement of the outputs of the temperature measuring devices give an accurate indication of the distribution of temperature on the surface of the blade. For example, the temperature measuring devices may be uniformly distributed over the entire exterior surface of the blade. They may be spaced about $\frac{1}{8}$ inch to $\frac{1}{4}$ inch apart. Two of these temperature measuring devices are labeled with reference numeral 9 in FIG. 2. Other measuring devices around the periphery of blade are illustrated in the cross section shown in FIG. 2.

An example of the temperature measuring devices is a series of wire thermocouples, which may be type K thermocouples that are capped, grounded, and insulated with MgO, and have a stainless steel or Inconel sheath. In this example of the invention, the thermocouples are embedded in grooves machined in the surface of the turbine blade.

As described in more detail below, the temperature of the blade's surface may be derived indirectly from a measurement of the surface temperature distribution on a heater attached to the surface of the blade. The temperature distribution on the surface of the heater may be measured in a variety of ways. These ways include using an infrared camera (FIGS. 3 and 4) to map the temperature distribution over the heater surface, treating the surface of the heater with a liquid crystal paint (FIG. 5) which changes color at a fixed known temperature, probing the heater surface with a temperature probe, and gluing a series of film thermocouples, such as those obtainable from RdF Corporation, to the surface of the heater.

In addition to the devices for measuring the temperature distribution on the surface of the blade, the apparatus of FIG. 1 includes a means for applying a known amount of heat flux to a predetermined surface area on the blade. It comprises a thin, foil-like, resistive heater 10, having a series of thin filamentary conductors distributed through a non-conductive sheet and connected to electrical leads 12. These heaters may be any of a variety of commercially available heater having these characteristics, for example, 50 ohm heaters obtainable from Minco, model number HK131118742.

The foil heater 10 covers the temperature measuring devices 11 and is attached to the surface of the turbine blade by way of glue or other bonding agent so that it makes intimate contact with that surface. The heater 10 is sized to cover a predetermined portion, preferably as close as possible to 100%, of the surface of turbine blade 14 which is normally exposed to hot gases flowing through the gas turbine engine. The method of attaching the heater to the surface of the turbine blade should be selected so that there is low thermal resistance between the conductors in the heater and the surface of the turbine blade covered by the heater.

As alluded to above, the temperature distribution on the surface of the blade may be inferred from the exterior surface temperature of the heater, that is, the temperature of the non-conductive material in which the heater filaments are sheathed. The surface temperature of the heater may be measured by a temperature measuring device 11, such as a film thermocouple, obtainable from, for example, RdF Corporation, attached to the surface of the heater as shown in FIGS. 1 and 2. The difference in temperature between the heater filaments and the surface of the blade may be derived from the known heat flux applied to the surface by the heater, which may be determined from the electrical power input to the heater and the area of the heater, and the thermal resistance between the heater and the blade's surface, which may be ascertained by using any generally known analytical technique.

When the temperature distribution is measured by using temperature measuring devices attached to the surface of the blade as shown in FIG. 2, a layer of insulation (not shown in the Figures) may be placed over the film heater 10 to direct heat normally flowing away from the turbine blade toward the surface of the turbine blade covered by the heater. When an infrared camera, liquid crystal, or temperature probe is used to measure the temperature distribution on the surface of the heater, no layer of insulation is used.

In the example of the invention shown in FIG. 1, the base of the turbine blade is installed in a rectangular opening in a flow fixture or inlet plenum 16. The space between the base of the blade and perimeter of the opening is filled with a sealant 17 to prevent the escape of cooling fluid through that space. The flow fixture 16 has an inlet port 18 for receiving cooling fluid, such as air, from a source of pressurized fluid not shown in FIGS. 1 and 2. Cooling fluid is supplied under pressure to the inlet port and from there into a series of cooling passages 20 beginning in the base of the blade and terminating at the top of the blade as shown in FIG. 1. The source of fluid is adjusted to provide a predetermined coolant flow rate at a preselected temperature to the cooling passages 20 or it is adjusted to provide a predetermined cooling fluid pressure and temperature at the inlet plenum. Any generally known source capable of supplying fluid under these conditions may be used.

Figure 8:
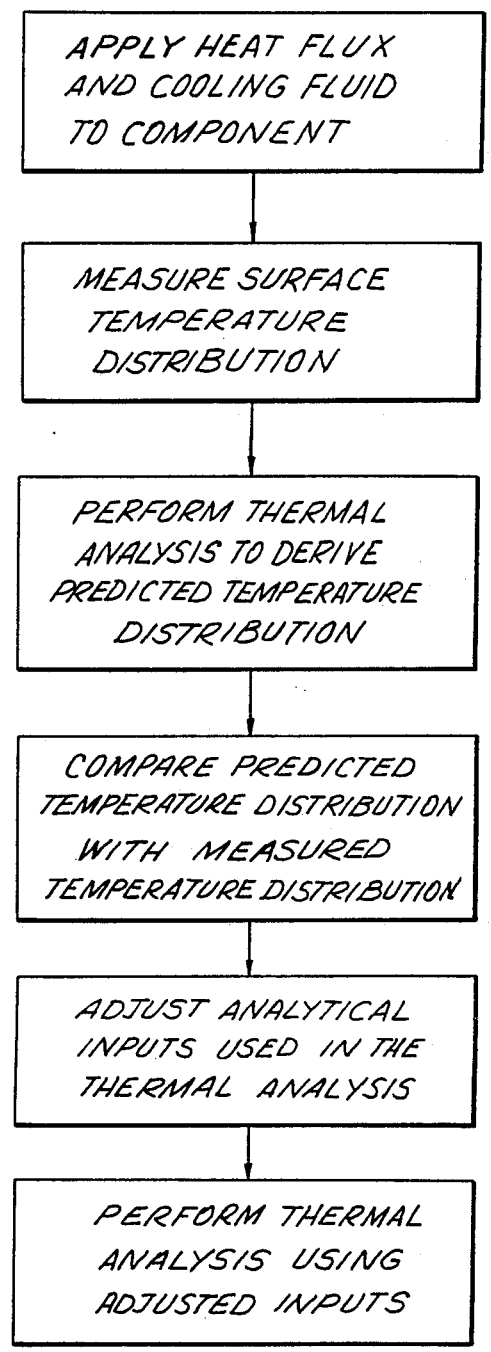
FIG. 8 is a flow chart illustrating the thermal performance checking procedure of the invention of this application.

After the turbine blade has been installed in the flow fixture, the thermal performance of the cooling circuit of the turbine blade may be checked as follows. The thermal performance check is illustrated in the flow chart of FIG. 8. First, cooling fluid flow having predetermined characteristics is introduced into the passages in the blade and a predetermined amount of heat flux is directed to the blade's surface. This may be accomplished by setting either the coolant flow rate and temperature or the coolant pressure and temperature and by setting the electrical power input to the heater. When steady state is reached, for example, after a few minutes, measurements may be taken while coolant and heat are being applied which can be used to determine the thermal performance of the cooling circuit. For example, the heater power, the coolant flow rate, the temperature and pressure of the coolant at the inlet of the flow fixture, the pressure and temperature of the coolant at the exit of the cooling passages in the blade, the temperature of the heater's exterior surface, and the temperature distribution on the surface of the blade may be measured. It is not important that all of these measurements be taken as long as they are the ones that are needed to derive appropriate data for checking the actual performance of the cooling circuit against design predictions.

One example of data which might be taken comprises the electrical power input to the heater, the temperature of the cooling fluid at the inlet to the flow fixture, the flow rate of the fluid into the fixture, and the temperature distribution over the surface of the blade. From the electrical power input to the heater and the area of the heater, the amount of heat flux supplied by the heater may be obtained. The temperature distribution gives important information about the thermal performance of the cooling circuit at the predetermined levels of coolant temperature and flow rate or pressure.

The thermal performance of the cooling circuit as a function of applied heat flux and coolant characteristics may thus be derived without having to install the blade in a gas turbine engine. To obtain some idea of how a component, such as the blade in FIG. 1, will fare in an operating engine, it is best to have this data for the conditions to be experienced by the component in such an operating engine. When it is not convenient to perform a thermal performance measurement at those conditions, as is most often the case, data may be taken at other conditions. That data may then be extrapolated to actual engine conditions.

The thermal performance of the cooling circuit, as indicated by the temperature distribution over the surface of the blade, may be compared with design predictions as soon as the blade is fabricated rather than after an engine is built, instrumented, and operated with the blade. Any discrepancy between the measured and the predicted surface temperatures is corrected by adjusting the analytical inputs to a thermal analysis, such as the commercially available ANSYS program from Swanson Analysis Systems of Houston, Pa., used to predict the thermal performance of the cooling circuit design under actual engine conditions. This discrepancy may be ascertained by performing a thermal analysis at the predetermined levels of surface heat flux and predetermined coolant flow conditions that are expected in the blade during a thermal performance measuring procedure in accordance with this invention. This analysis results in a calculated prediction of the surface temperature distribution for the blade during the thermal performance measuring conditions. The calculated temperatures from the thermal analysis and the measured temperatures from an actual thermal measurement performed at the levels of surface heat flux and coolant flow used in the thermal analysis are compared, and, if there is any disagreement, the analytical inputs used in the analysis, for example, assumed heat transfer coefficients distributions, are modified so that there is agreement between the measured temperatures and the predicted temperatures. A thermal analysis at actual conditions existing in an operating engine, which often are much different from the conditions of the thermal performance measuring procedure (where measured temperatures on the surface of a turbine blade might not exceed 300 degrees Fahrenheit, whereas the temperatures in an engine might be on the order of 2000 degrees Fahrenheit), then may be performed using the modified analytical inputs. In this way, a prediction of the blade's temperature distribution at engine conditions may be made based on actual thermal performance of the cooling circuit. This is a simple and accurate way of making sure the design of the cooling circuit is adequate when the component is installed and operated in an engine.

In addition to making predictions of thermal performance at engine conditions, a discrepancy between the measured and calculated temperatures may also be a basis for redesigning the cooling circuit so that it accomplishes the aims for which the cooling circuit is being designed.

In a production situation, the result of the thermal check described here may be used to monitor the adequacy of the processes for making the components which are the subject of the thermal check. Any components made in accordance with the process and having a defective cooling circuit will be identified when measured temperature distributions do not agree with expected temperature distributions.

Other components besides the cooled turbine blade shown in FIGS. 1 and 2 may be the subject of the thermal check of this application. Among other things, the invention is applicable to any component of machinery which is cooled. It is particularly applicable to components having internal passages for the flow of cooling fluid, such as blades, vanes, and shrouds in a gas turbine engine. It may also be used to check the performance of cooling circuits which involve blowing cooling fluid over exterior surfaces of the component being tested. All that is needed is a way of applying a coolant flow having predetermined characteristics to the component, applying a predetermined amount of heat flux to the component, and measuring a temperature distribution on a surface of the component.

Figure 6:
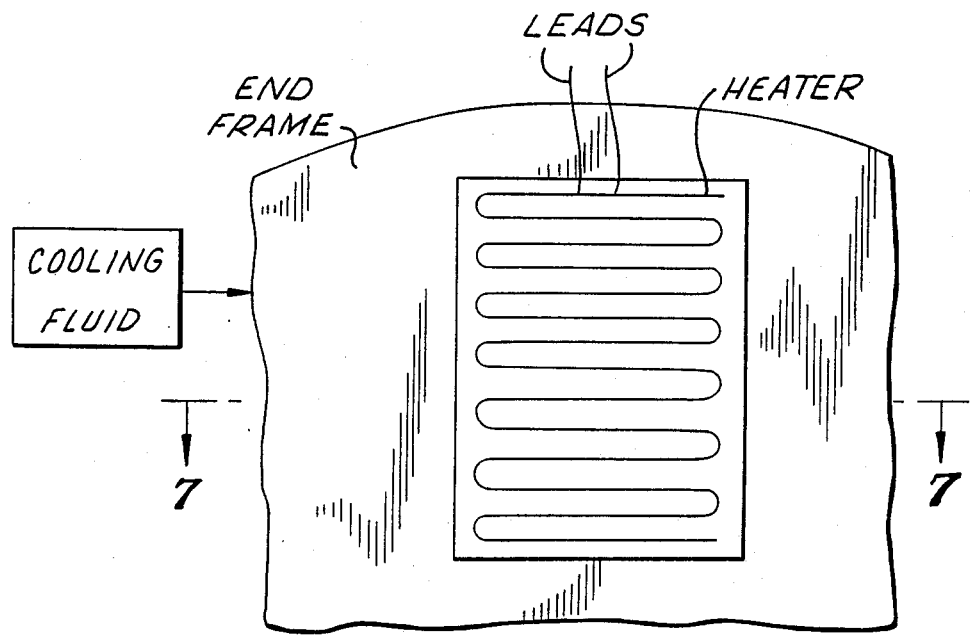
FIGS. 6 and 7 are a schematic front view and a schematic cross section, respectively, of a rear frame, sometimes referred to as an end frame, of a gas turbine engine, to which the thermal performance checking procedure disclosed in this application may be applied.
Figure 7:
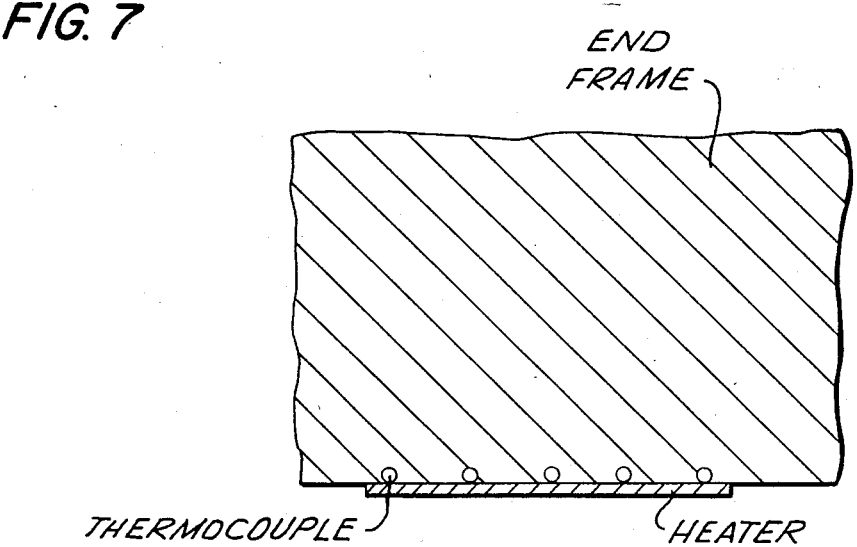

The thermal check described in this application may also be applied to a situation involving a component having an internal or external circuit for heating the component. For example, it is applicable to a component such as the rear or end frame of the turbine in a gas turbine engine. See FIGS. 6 and 7. Such a frame has internal passages through which heated fluid may flow so that the thermal expansion and contraction of the frame may be controlled. The thermal check is also applicable to engine components used to control the clearance between blade tips and casings.

When checking the performance of the heating circuit or verifying the adequacy of a manufacturing process involving such a heating circuit, the same procedure described above for measuring the thermal performance of cooled components is used. In one example, a known amount of heat flux is applied to the component by means of varying the electrical power input to a heater attached to a predetermined surfaces of the component. A cooling fluid flow having predetermined characteristics is introduced into the heating circuit and the temperature distribution over a preselected surface is then measured in a manner like that described for cooled components. The measured temperature distribution is an indication of the thermal performance of the heating circuit design, as in the case of a cooled component as described above. Even though the direction of heat flow under the test conditions is opposite to that in actual operating conditions, no significant error is involved in determining thermal performance of heating circuits by using this invention.

I claim:

1. An apparatus for measuring the thermal performance of a component, comprising:
    a means for applying a predetermined amount of heat flux to a predetermined outer surface of the component;
    a means for applying a cooling fluid flow having predetermined characteristics to the component and
    a means for measuring a temperature distribution on a preselected surface of the component while the predetermined amount of heat flux and the cooling fluid flow having predetermined characteristics are being applied to the component.

2. The apparatus of claim 1, in which the means for applying a predetermined amount of heat flux comprises a resistive, foil heater attached to the predetermined surface of the component.

3. The apparatus of claim 1, in which the means for measuring a temperature distribution comprises a plurality of thermocouples attached to the preselected surface of the component.

4. The apparatus of claim 3, in which the thermocouples are embedded in the preselected surface of the component.

5. The apparatus of claim 3, in which the means for applying a predetermined amount of heat flux comprises a resistive, foil heater covering the thermocouples and a means for varying the electrical power input to the resistive, foil heater.

6. The apparatus of claim 1, in which the means for measuring a temperature distribution comprises a means for measuring a temperature distribution on a predetermined surface of the heat flux applying means.

7. The apparatus of claim 6, in which the means for measuring a temperature distribution on a predetermined surface of the heat flux applying means comprises film thermocouples attached to a predetermined surface of the heat flux applying means.

8. The apparatus of claim 6, in which the means for measuring the temperature distribution on a predetermined surface of the heat flux applying means comprises an infrared camera.

9. The apparatus of claim 6, in which the means for measuring the temperature distribution on a predetermined surface of the heat flux applying means comprises a liquid crystal attached to a predetermined surface of the heat flux applying means.

10. The apparatus of claim 1, in which the means for applying cooling fluid flow to the component comprises a means for applying cooling fluid to the component at a predetermined temperature and flow rate.

11. The apparatus of claim 1, in which the means for applying cooling fluid flow to the component comprises a means for applying cooling fluid to the component at a predetermined temperature and pressure.

12. The apparatus of claim 1, in which the component contains one or more internal passages for the flow of fluid and in which the means for applying cooling fluid flow to the component directs a cooling fluid flow through the passages in the component 13. The apparatus of claim 12, in which the passages are cooling passages.

14. The apparatus of claim 12, in which the passages are heating passages.

15. The apparatus of claim 1, in which the component is a turbine engine component.

16. The apparatus of claim 1, in which the component is a cooled component in a gas turbine engine.

17. The apparatus of claim 1, in which the component is a heated component in a gas turbine engine.

18. The apparatus of claim 1, in which the component is a turbine blade having internal cooling passages.

19. The apparatus of claim 1, in which the component is the rear frame of the turbine in a gas turbine engine.

20. A method of measuring the thermal performance of a component, comprising the steps of:
    applying a predetermined amount of heat flux to a predetermined outer surface of a component;
    applying a cooling fluid flow having predetermined characteristics to the component; and
    measuring a temperature distribution on a preselected surface of the component while the predetermined amount of heat flux and the cooling fluid flow having predetermined characteristics are being applied to the component.

21. The method of claim 20, in which the step of applying heat flux to a predetermined surface of the component comprises the step of attaching a resistive, foil heater to the predetermined surface of the component and applying a predetermined amount of electrical power to the resistive, foil heater.

22. The method of claim 20, in which the measuring step comprises attaching a number of thermocouples to the preselected surface of the component and measuring the outputs of the thermocouples.

23. The method of claim 22, in which the attaching step comprises embedding the thermocouples in the preselected surface of the component.

24. The method of claim 22, in which the step of applying a predetermined amount of heat flux to a predetermined surface of the component comprises covering the thermocouples with a resistive heater and varying the electrical power input to the resistive heater.

25. The method of claim 20, in which the measuring step comprises the step of measuring the temperature distribution over a predetermined surface of a heater used to apply the predetermined amount of heat flux to the predetermined surface of the component.

26. The method of claim 25, in which the step of measuring the temperature distribution over a predetermined surface of a heater comprises the step of applying film thermocouples to the predetermined surface of the heater and measuring the output of the thermocouples.

27. The method of claim 25, in which the step of measuring the temperature distribution over a predetermined surface of a heater comprises the step of mapping the temperature distribution over the predetermined surface of the heater with an infrared camera.

28. The method of claim 25, in which the step of measuring the temperature distribution over a predetermined surface of a heater comprises the step of attaching a liquid crystal to the predetermined surface of the heater and observing the color of the liquid crystal.

29. The method of claim 20, in which the step of applying cooling fluid flow to the component comprises the step of directing cooling fluid to the component at a predetermined temperature and flow rate.

30. The method of claim 20, in which the step of applying cooling fluid flow to the component comprises the step of directing cooling fluid to the component at a predetermined temperature and pressure.

31. The method of claim 20, in which the step of applying a cooling fluid flow to the component comprises the step of applying the cooling fluid flow through one or more passages in the component.

32. The method of claim 31, in which the passages are cooling passages.

33. The method of claim 31, in which the passages are heating passages.

34. The method of claim 20, in which the component is a turbine engine component.

35. The method of claim 20, in which the component is a cooled component in a gas turbine engine.

36. The method of claim 20, in which the component is a heated component in a gas turbine engine.

37. The method of claim 20, in which the component is a turbine blade containing internal cooling passages.

38. The method of claim 20, in which the component is the rear frame of the turbine in a gas turbine engine.

39. The method of claim 20, further comprising the steps of:
performing a thermal analysis based on the predetermined amount of heat flux and the predetermined characteristics of the cooling fluid flow to derive a predicted temperature distribution;
comparing the predicted temperature distribution with the measured temperature distribution; and
adjusting one or more analytical inputs used in the thermal analysis based on the comparing step.

40. The method of claim 39, further comprising the step of performing a thermal analysis using the adjusted analytical inputs.

41. The method of claim 40, in which the thermal analysis using the adjusted analytical inputs is based on expected conditions to be experienced by the component in actual operation.

42. The method of claim 39, in which the analytical inputs include a heat transfer coefficient distribution.

* * * * *